United States Patent [19]
Chuter

[11] Patent Number: 5,833,699
[45] Date of Patent: Nov. 10, 1998

[54] EXTENDING RIBBON STENT

[76] Inventor: Timothy A. M. Chuter, 2209 Abeline Dr., Burlingame, Calif. 94010

[21] Appl. No.: 629,828

[22] Filed: Apr. 10, 1996

[51] Int. Cl.⁶ ................................................. A61M 25/00
[52] U.S. Cl. ............................... 606/198; 623/1; 623/12
[58] Field of Search ............................. 606/1, 108, 191, 606/194, 192, 198, 200; 623/1, 12

[56] References Cited

U.S. PATENT DOCUMENTS

| | | |
|---|---|---|
| 4,214,587 | 7/1980 | Sakura, Jr. . |
| 4,503,569 | 3/1985 | Dotter . |
| 4,553,545 | 11/1985 | Maass . |
| 4,580,568 | 4/1986 | Granturco . |
| 4,655,771 | 4/1987 | Wallsten . |
| 4,733,665 | 3/1988 | Palmaz . |
| 4,739,762 | 4/1988 | Palmaz . |
| 4,787,899 | 11/1988 | Lazarus . |
| 4,820,298 | 4/1989 | Leveen et al. . |
| 4,830,003 | 5/1989 | Wolff et al. . |
| 4,886,062 | 12/1989 | Wiktor . |
| 4,913,141 | 4/1990 | Hillstead . |
| 4,990,155 | 2/1991 | Wilkoff . |
| 5,015,253 | 5/1991 | MacGregor . |
| 5,019,085 | 5/1991 | Hillstead . |
| 5,019,090 | 5/1991 | Pinchuk . |
| 5,037,427 | 8/1991 | Harada et al. . |
| 5,104,404 | 4/1992 | Wolff . |
| 5,133,732 | 7/1992 | Wiktor . |
| 5,135,536 | 8/1992 | Hillstead . |
| 5,192,307 | 3/1993 | Wall . |
| 5,222,971 | 6/1993 | Willard et al. . |
| 5,226,913 | 7/1993 | Pinchuk . |
| 5,316,023 | 5/1994 | Palmaz et al. . |
| 5,331,027 | 7/1994 | Whitbourne . |
| 5,342,348 | 8/1994 | Kaplan . |
| 5,342,387 | 8/1994 | Summers . |
| 5,366,504 | 11/1994 | Andersen et al. . |
| 5,370,683 | 12/1994 | Fontaine . |
| 5,383,892 | 1/1995 | Cardon et al. . |
| 5,383,925 | 1/1995 | Schmitt . |
| 5,415,664 | 5/1995 | Pinchuk . |
| 5,423,885 | 6/1995 | Williams . |
| 5,441,515 | 8/1995 | Khosravi et al. . |
| 5,443,907 | 8/1995 | Slaiken et al. . |
| 5,474,563 | 12/1995 | Myler et al. . |
| 5,476,508 | 12/1995 | Amstrup . |
| 5,490,839 | 2/1996 | Wang et al. . |
| 5,507,767 | 4/1996 | Maeda et al. . |
| 5,514,154 | 5/1996 | Lau et al. . |
| 5,527,354 | 6/1996 | Fontaine et al. . |
| 5,527,355 | 6/1996 | Ahn . |
| 5,540,712 | 7/1996 | Kleshinski et al. . |
| 5,549,663 | 8/1996 | Cottone, Jr. . |
| 5,562,726 | 10/1996 | Chuter . |
| 5,571,170 | 11/1996 | Palmaz et al. . |
| 5,591,197 | 1/1997 | Orth et al. . |
| 5,591,228 | 1/1997 | Edoga . |
| 5,603,721 | 2/1997 | Lau et al. . |
| 5,609,627 | 3/1997 | Goicoechea et al. . |
| 5,613,979 | 3/1997 | Trotta et al. . |
| 5,617,878 | 4/1997 | Taheri . |
| 5,628,782 | 5/1997 | Myers et al. . |
| 5,628,788 | 5/1997 | Pinchuk . |
| 5,630,829 | 5/1997 | Lauterjung . |
| 5,632,763 | 5/1997 | Glastra . |
| 5,645,532 | 7/1997 | Horgan . |
| 5,649,949 | 7/1997 | Wallace et al. . |
| 5,649,951 | 7/1997 | Davidson . |
| B1 4,733,665 | 2/1988 | Palmaz . |

OTHER PUBLICATIONS

Description of Hexstent by Applicant, T.A.M. Chuter.

*Primary Examiner*—William Lewis
*Attorney, Agent, or Firm*—William G. Lane

[57] ABSTRACT

The present invention concerns an improved stent for placement in corporeal lumens. More particularly, the present invention concerns an improved stent for placement in a corporeal lumen comprising a coiled ribbon which is rigid enough to maintain the relative position of each turn of the coiled ribbon during its expansion within the lumen after placement.

26 Claims, 3 Drawing Sheets

COMPRESSED

EXPANDED

COMPRESSED

COMPRESSED

PARTIALLY EXPANDED

FULLY EXPANDED

EXTENSION

COMPRESSED

EXPANDED

OBLIQUE CONNECTOR (10)

EXTENDING RIBBON STENT

FIELD OF THE INVENTION

The present invention relates to an improved stent for placement in corporeal lumens. More particularly, the present invention relates to an improved stent for placement in a corporeal lumen comprising a coiled ribbon which is rigid enough to maintain the relative position of each turn of the coil during its expansion within the lumen after placement.

BACKGROUND OF THE INVENTION

The term stent generally refers to a prosthesis, which can be introduced into a corporeal lumen and expanded to support that lumen or attach a conduit to the inner surface of that lumen. Since most lumens are roughly circular in cross-section, so are most stents. But the stent should not be a rigid cylinder, because few lumens are straight; all but the shortest stents need some element of flexibility. The long axis of the stent must be able to bend in order to follow the long axis of the lumen.

The flexibility of any tubular structure depends on the ease with which the stent structure can accommodate changes in the relative lengths of its inner and outer walls; a stent is no exception. If the stent bends smoothly, its outer wall will always be longer than its inner wall, to a degree which is proportional to the width of the stent and inversely proportional to the radius of curvature. The flexibility of a stent is determined by the extent to which its structure can accommodate the necessary length discrepancy.

In general, a stent with many longitudinally oriented structural elements is rigid because the structural elements impose their fixed length on the length of the stent wall. More transversely oriented structural elements do not have this effect, because small changes in the angles between them can produce large changes in stent length. In addition, any joining of stent elements, that limits their freedom in a direction parallel to the long axis of the stent, will also reduce stent flexibility. Therefore, the most flexible stents are those in which the structural elements are oriented transversely, and there are no longitudinal connections.

Since all stents expand by changing the orientation of their structural elements from longitudinal to transverse, it is possible to maximize flexibility of a stent by expanding it to the highest degree, thereby maximizing the transverse orientation of the structural elements. Unfortunately, this degree of stent expansion may compromise the structural integrity of the stent by over-deforming the junctions between stent elements. The only stents that are not subject to this constraint consist of one or more coil shaped elements, which may be intertwined, but are not joined. Examples include the stents described by Willard, (U.S. Pat. No. 5,222,971); Harada et al, (U.S. Pat. No. 5,037,427); Dotter, (U.S. Pat. No. 4,503,569); Wilkoff, (U.S. Pat. No. 4,990,155); Maas, et al (U.S. Pat. No. 4,553,545); Wallsten, (U.S. Pat. No. 4,655,771). When fully expanded, with the adjacent coils almost touching, these stents are as flexible as a Slinky.

Unfortunately, this flexibility comes at a price. Since the structural element that forms the coil has a fixed length, and high degrees of stent expansion must be accompanied by large reductions either in the number of turns or in the length of the stent. Winding the stent into a compressed state is possible, but is limited by the resultant tension. Moreover, the unwinding of a stent during delivery precludes pre-attachment to an unwound prosthesis such as a fabric, which is often deemed desirable by the user. Such unwinding is also difficult to control and can be damaging to the inner surface of the corporeal lumen. For these reasons, stent shortening tends to be the primary means of stent expansion for this type of stent. Therefore, the more flexible coil stents tend to be much shorter when expanded than they are in the fully compressed state. This degree of shortening complicates stent delivery, particularly if the stent is to be used inside a lumen of uncertain diameter, or in conjunction with a prosthesis of a fixed length, such as a fabric.

A third alternative is to make the structural element of the coil variable in length. The additional length required to encircle the expanded stent comes from extension of the coil element. Several manifestations of this approach currently exist. They include the stents described by Hillstead, (U.S. Pat. No. 5,019,085) and Wiktor (U.S. Pat. No. 5,133,732). All stents of this type have the same basic structure, and all suffer from the same basic problem, irrespective of whether expansion is driven by a balloon or by the elasticity of the material; the zig-zag wire that forms the coil can twist and bend in any direction, making the stent structurally unstable. The resultant gaps and luminal impingement can be prevented by linking adjacent turns of the coil, but his limits the flexibility of the stent.

A number of prior art references are available in the art, each of which references are directed to some specific discreet elements of the system which is described and claimed in the present invention, however, none of which is directed to the totality of the combination, or its use and function in the manner described and claimed herein.

The following prior art references are known to the inventor:

U.S. Pat. No. 4,503,569, which issued to Dotter on Mar. 12, 1985 describes a transluminally placed endovascular graft prosthesis which includes a helically wound coil having a generally tubular shape and is made of a shape memory Nitinol alloy having a transition temperature in the range of 115°–125° F. After placement within a body blood vessel and upon heating of the prosthesis to its transition temperature, the prosthesis expands so as to become firmly anchored to the inside wall of the body blood vessel.

U.S. Pat. No. 4,553,545, which issued to Maas et al in November 1985, is directed to a spiral stent composed of a flat (non-extending) ribbon, or parallel connected ribbons of steel.

U.S. Pat. No. 4,655,771, which issued to Wallsten on Apr. 7, 1987, teaches a prosthesis for transluminal implantation comprising a flexible tubular body which has a diameter that is variable by axial movement of the ends of the body relative to each other and which is composed of several individual rigid but flexible thread elements each of which extends in helix configuration with the centerline of the body as a common axis;

U.S. Pat. No. 4,739,762, which issued to Palmaz on Apr. 26, 1988, teaches an expandable intraluminal graft for use within a body passageway or duct which is particularly useful for repairing blood vessels which have been narrowed or occluded by disease;

U.S. Pat. No. 4,990,155, which issued to Wilkoff on Feb. 5, 1991 is directed to a method for preventing arterial restenosis after angioplasty which includes the steps of providing a base coil of a substantially uniform diameter, inducing in the base coil an elastic memory that provides an inherent tendency to return to the given diameter after any distortion, forming from the base coil a coil stent with a substantially uniform predetermined diameter substantially less than the given diameter, releasably coupling the coil stent to an elongated delivery device adapted to pass through a blood carrying vessel, inserting the coil stent and delivery device into a vessel, and manipulating the delivery device within the vessel so as to position the coil stent at a desired location therein.

U.S. Pat. No. 5,019,085, which issued to Hillstead on May 28, 1991, relates to a stent delivery system and method wherein a delivery wire is routed out an opening in a delivery catheter and looped over a portion of the stent and then routed back inside the delivery catheter. At an extreme distal end of the stent, the wire again exits the delivery catheter center passageway. This compresses the stent into a form whereby the delivery catheter can be maneuvered through a vessel to position the stent. To release the stent from the delivery catheter, the delivery wire is retracted so that its distal end passes out both pair of openings in the delivery catheter allowing the stent to expand into engagement with the vessel wall.

U.S. Pat. No. 5,037,427, which issued to Harada et al on Aug. 6, 1991, teaches an instrument for expanding a tubular organ such as a blood vessel and for keeping the tubular organ expanded for a predetermined period of time, and a catheter for mounting said instrument at a desired position within the tubular organ, said catheter being capable of moving and recovering the instrument mounted within the tubular organ. The instrument is formed of a two-way shape memory alloy and expands or shrinks in the radial direction, in accordance with changes in temperature.

U.S. Pat. No. 5,133,732, which issued to Wiktor on Jul. 28, 1992, discloses a stent for implantation into a body vessel comprising a cylindrical stent body which has been coiled from a generally continuous wire which has been imparted with a deformable zig-zag structure;

U.S. Pat. No. 5,222,971, which issued to Willard et al on Jul. 29, 1993 teaches a temporary stent for supporting a region of a vessel in a body comprising a stent portion and an actuator portion and methods for the use and manufacture thereof. The stent portion is comprised of an elongate perfusable vessel supporting portion adapted to be configurable between a reduced size for placement in the vessel and between a reduced size for placement in the vessel and removal therefrom and an expanded size for structurally supporting the vessel and perfusable end portions connected to and forming ends of the vessel supporting portion and adapted to allow fluid flow therethrough.

U.S. Pat. No. 5,370,683, which issued to Fontaine on Dec. 6, 1994, is directed to a vascular stent for reducing hemodynamic disturbances caused by angioplasty, said stent being formed from a single filament of low memory biocompatible material having a series of U-shaped bends. The filament is wrapped about a mandril in a circular fashion in order to align the curved portions of each bend which may then be connected;

None of the foregoing references in any way teaches the advantages to be achieved by utilizing the coiled ribbon stent of the present invention.

It is, therefore, an objective of the present invention to provide for an improved stent which exhibits superior structural stability, as compared to other available prior art stents, when inserted into a corporeal lumen.

It is a further object of the present invention to provide for an improved stent which comprises an extending ribbon wherein the ribbon maintains the relative position of each turn of each coil during the process of expansion.

It is a further object of the present invention to provide for an extending ribbon stent which allows for an increase in the diameter of the stent without any appreciable change in the overall length of the stent or in the number of turns of the coiled stent structure.

Lastly, it is an object of the present invention to provide for an improved stent which comprises a coiled ribbon structure which may be either self-expanding or balloon expanding.

These and other objects of the invention will become apparent from the following discussion of the invention.

SUMMARY OF THE INVENTION

The present invention provides for an improved stent for placement in corporeal lumens. The instant invention relies upon utilization of a coiled ribbon which has sufficient structural rigidity to extend when placed within a corporeal lumen and, at the same time, retain the relative position of each turn or curve which has been incorporated into the coiled ribbon structure.

The problems discussed above are solved by making a coiled stent from an extending ribbon, which is rigid enough to maintain the relative position of each turn, of each coil during expansion within the lumen. The diameter of the extending coiled ribbon stent of the present invention increases without any substantial change in the overall length of the stent, or in the number of turns of the coil. The only change is in the length of the ribbon itself. Ribbon elongation is accomplished by the same kind of configurational change through which any other stent expands; structural elements are rotated away from the long axis of the stent into a more transverse orientation.

The construction and obvious advantages of the system provided for by the present invention will be more clearly understood from the following description of the various specific embodiments when read in conjunction with the accompanying drawings.

Figure 4A:
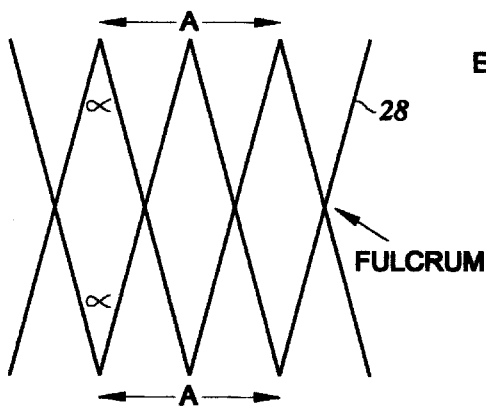
FIG. 4a is a schematic representation of an optional additional layer of the ribbon structure of the coiled ribbon stent according to the present invention, such structure incorporating longer, more rigid struts in the ribbon layer, showing the ribbon layer in the compressed position.

Fib. 4c is a schematic representation of the structure of the FIG. 4a showing the longer struts having a thicker profile which is unaffected by the action of the stent expansion.

Figure 5:
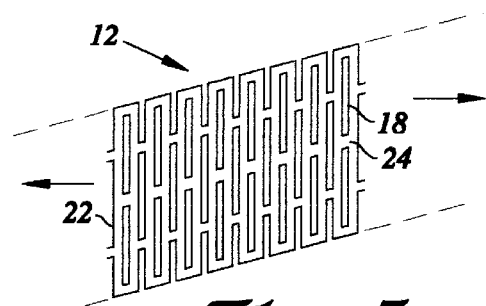

FIG. 5 is a schematic representation depicting a preferred embodiment of a simple lattice design for the ribbon structure which produces purely transaxial expansion.

Figure 6:
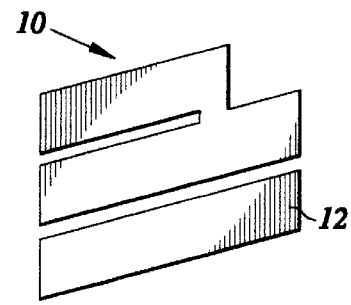

FIG. 6 is a schematic representation of the terminal loop of a preferred embodiment of the ribbon structure of the present invention.

Figure 7A:
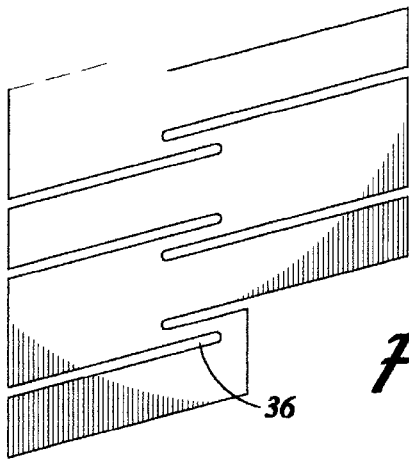

FIG. 7a is a schematic representation of yet another preferred embodiment of the ribbon structure of the present invention showing the ribbon in a compressed position.

Figure 7B:
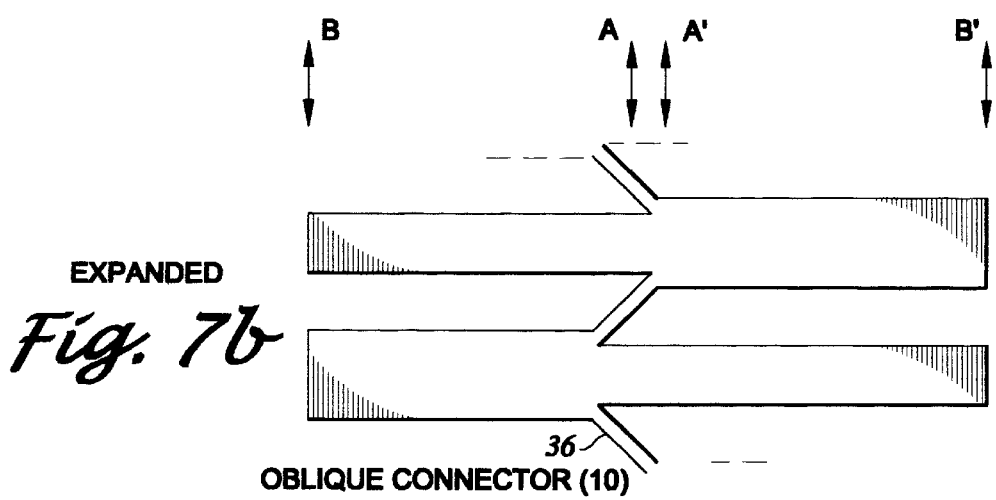

FIG. 7b is a schematic representation of yet another preferred embodiment of the ribbon structure of the present invention showing the ribbon in an expanded position.

DETAILED DESCRIPTION OF THE INVENTION

The present invention is directed to an improved "stent" for placement in corporeal lumens. More particularly, the present invention is directed to an improved stent for placement in a corporeal lumen comprising a coiled ribbon which is rigid enough to maintain the relative position of each turn of the coil during its expansion within the lumen after placement.

With reference to FIGS. 1–7, it will be appreciated that the longitudinal stability of the stent of the present invention depends on each turn of the coil maintaining its approximate position relative to its neighbors. To do this, the axial orientation of the ribbon must be substantially constant relative to the long axis of the stent. There can be little bending of the ribbon up or down the surface of the stent. In order for the ribbon to bend in this direction, its two edges would have to be capable of differential elongation. Therefore, limitation of differential elongation between these edges is a key design feature, in that it imbues the ribbon with the necessary rigidity, and the stent with the necessary stability. To achieve this goal, a single strip of metal may be etched to form a lattice, or zig-zag wires may be braided to form a flat mesh.

Figure 1A:
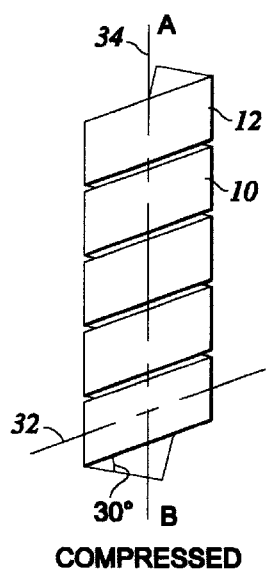
FIG. 1a is a schematic representation of a coiled ribbon stent according to the present invention showing the stent in the compressed position.
Figure 1B:
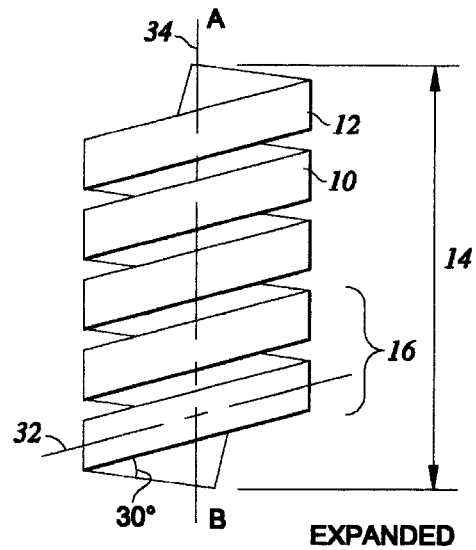
FIG. 1b is a schematic representation of the coiled ribbon stent according to the present invention showing the stent in the expanded position.

With reference to FIGS. 1(a)–1(b), which depict the stent 10 of the present invention in compressed and expanded views respectively, which stent comprises a coiled ribbon 12 having a defined length which defines the overall length 14 of the coiled stent, which overall length of the coiled stent remains relatively constant from the compressed position to the expanded position. In order to maintain the aforementioned overall length relatively constant from the compressed to the expanded position, each turn 16 of the coil ribbon must retain its approximate relative position with relation to each of its adjacent neighboring turns.

Figure 2A:
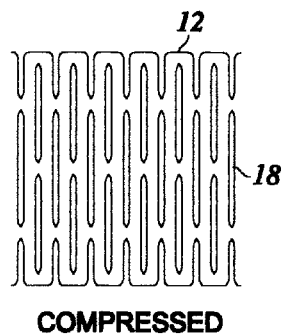
FIG. 2a is a schematic representation of one preferred embodiment of a lattice structure forming the ribbon of the coiled ribbon stent of the present invention showing a portion of the ribbon in the compressed position.
Figure 2C:
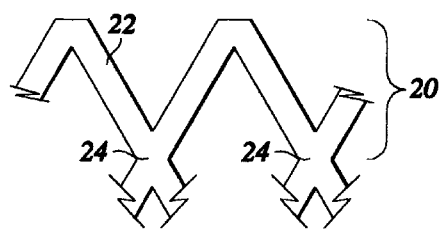
FIG. 2c is a schematic representation depicting an enlarged view of one chain of the extended ribbon structure shown in FIG. 2b.
Figure 2B:
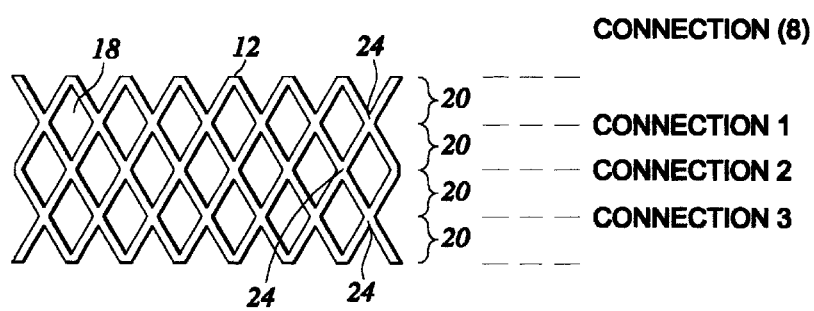
FIG. 2b is a schematic representation of one preferred embodiment of a lattice structure forming the ribbon of the coiled ribbon stent of the present invention showing the ribbon in an extended position.

With reference to FIGS. 2(a)–2(c), which depict a preferred embodiment of the structure of the ribbon element of the coiled ribbon stent of the present invention, a portion of the ribbon 12 element is shown in FIG. 2(a) in the compressed position and appears as an etched lattice 18 having an alternating offset series of elongated slots in the compressed configuration. In the expanded configuration depicted in FIG. 2(b), it can be seen that the lattice 18 in this embodiment consists of four zig-zag chains 20, a portion of one of which chains is depicted in FIG. 2c. Each chain comprises a series of struts 22 which are joined at their points of contact in three lines of connections 24. The etching and method of expansion, shown in the embodiment depicted in FIGS. 2(a)–2(c), resemble those seen in the wall of a Palmaz stent, U.S. Pat. No. 4,739,762; the difference being that while the present invention is a flat ribbon, the Palmaz stent is a cylinder.

It will be appreciated by one skilled in the art that many alternative configurations are possible and can differ from the precise lattice configuration depicted in FIGS. 2(a)–2(c), depending on the actual shapes and spacing of the slots that are etched into the ribbon.

As described above, the rigidity of the ribbon depends on the limitation of differential elongation between its two edges. Since any change in strut 22 orientation produces more elongation when the ribbon is at the collapsed end of its compression range, and less when it is at the extended end of its compression range, the potential for differential elongation, diminishes as the ribbon reaches full extension.

Figure 3A:
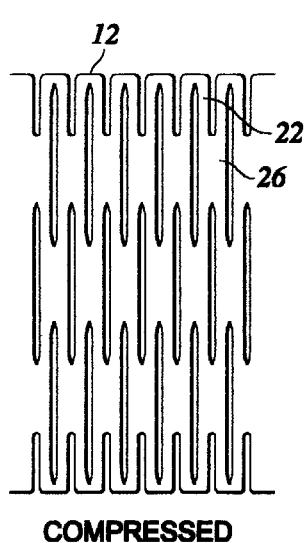
FIG. 3a is a schematic representation of another preferred embodiment of a lattice structure forming the ribbon of the coiled ribbon stent of the present invention showing a portion of the ribbon in the compressed position.
Figure 3B:
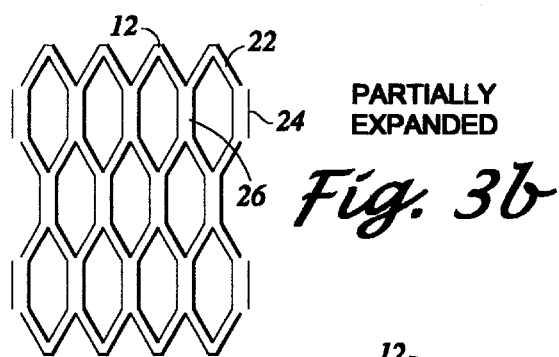
FIG. 3b is a schematic representation of one preferred embodiment of a lattice structure forming the ribbon of the coiled ribbon stent of the present invention showing the ribbon in a partially extended position.
Figure 3C:
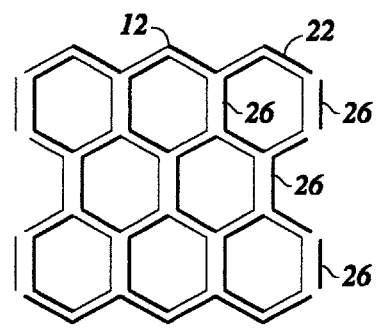
FIG. 3c is a schematic representation of one preferred embodiment of a lattice structure forming the ribbon of the coiled ribbon stent of the present invention showing the ribbon in a fully extended position.

An important factor in ribbon stability is the separation between the chains of struts that comprise the structural elements of its two edges. The wider the separation, the greater the differential elongation for any given degree of bending. Therefore, the wider the ribbon, the less it is likely to bend. With reference to FIGS. 3(a) to 3(c), which depict an alternative preferred embodiment of the lattice structure of the ribbon element comprising the coiled ribbon stent of the present invention, and presents a more stable version of the ribbon which is produced by introducing spacers 26 along the line of connections 24 between the chains 20 of struts 22. This allows the ribbon to be extended to the point where the struts 22 are almost parallel to the long axis of the ribbon, while retaining some separation between the chains 20 that form the edges of the ribbon.

Figure 4B:
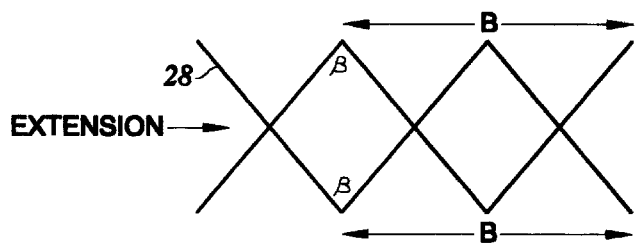
FIG. 4b is a schematic representation of an optional additional layer of the ribbon structure of the coiled ribbon stent according to the present invention, such structure incorporating longer, more rigid struts in the ribbon layer, showing the ribbon layer in the extended position.
Figure 4C:
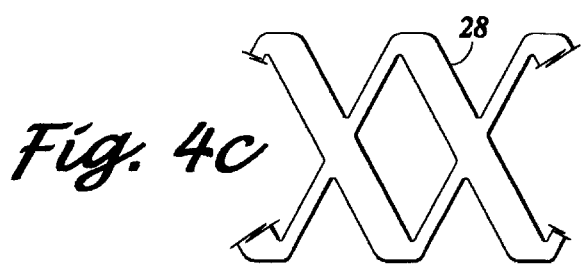

Once the ribbon reaches the configuration shown in FIG. 3c, it is very rigid, and the stent is very stable. However, the expanding (FIGS. 3a and 3b) stent is less stable. This characteristic is not a problem with versions of the stent intended for balloon-expansion, because the balloon bulges between the turns of the coil and maintains their relative positions. However, self-expanding versions need to be constructed in a way that maximizes stability. One way to do this is to widen the ribbon, as discussed above. Another alternative way of maximizing stability is to add one or more layers of longer, more rigid struts 28 to the ribbon lattice structure as depicted in FIGS. 4(a)–4c). The layer of longer, more rigid struts extends from one edge of the ribbon to the other, and ensures that the changes in strut orientation, and accompanying changes in length, are equal on both edges of the ribbon. FIG. 4(c) shows that one set of long struts 28 can be created by changing the etch pattern of the ribbon element to create a thicker strut that is unaffected by the deformation of stent expansion. The other set of struts has to be created separately and bonded to the lattice.

The orientation of the lattice has an important effect on the length of the stent. As seen in FIG. 1, the angle 30 between the long axis 32 of the ribbon 12 and the long axis 34 of the stent 10 needs to fall, if the stent is to remain at the same overall length throughout expansion. A lattice, formed by slots perpendicular to the long axis of the ribbon, will produce extension of the ribbon directly along its long axis. This would mean that the long axis of the ribbon would remain at a constant angle to the long axis of the stent, and the stent would elongate as it expanded, which may be undesirable. To maintain constant stent length, the plane of ribbon elongation needs to be perpendicular to the long axis of the stent.

A preferred embodiment of a lattice designed to produce purely trans-axial expansion is illustrated in FIG. 5. The narrowing of the ribbon, associated with stent expansion, has no effect on overall stent length so long as the axial orientation of the ribbon remains constant. The space between adjacent turns of the coil just increases, while maintaining a constant relative position between adjacent coil turns.

The advantages of the extending ribbon coil stent design, which are flexibility and a stable length, are present whether the stent is self-expanding or balloon expanded, and the same basic construction can be used for both types of stent; the main difference residing the mechanical properties of the metal. If the stent changes configuration by elastic deformation, it is self-expanding, and if it changes configuration by plastic deformation, it is balloon-expanded.

The balloon-expanded version differs in one other regard; the terminal loop must be closed, rather than open, as it is in the self-expanding stent. If the coil in a balloon-expanded stent were left open, it would tend to bend outward and unwind slightly, instead of elongating. Following balloon deflation, the coil end would tend to return to its former position, resulting in incomplete expansion of both ends of the stent. Therefore, in order to ensure full expansion of the coiled stent in such a situation, the last turn of the coil must be closed, as depicted in FIG. 6, by joining the end of the ribbon to the adjacent ribbon segment. This prevents unwinding and ensures full ribbon elongation.

The stent coil can be formed either by wrapping an extendible ribbon around a cylindrical form or, alternatively, for example, by etching one or more spiral slots into a single cylinder of metal. The spiral slots divide adjacent turns of the stent creating a coil. This method of construction is particularly applicable to the construction of balloon-expanded versions of the stent, in which the last turns of the coil must be closed. In this case, the spiral slots end before they exit the end of the metal cylinder, thereby closing the last turn of the coil, see FIGS. 7(a)–7(b) which depict a preferred embodiment of one type of spiral coil in the compressed and expanded configuration, respectively.

Other turns of the coil can also be linked in this way to increase stability. The resultant loss of flexibility can be minimized by offsetting and overlapping the spiral slots slightly as depicted in FIGS. 7(a)–7(b). The resulting oblique connectors 36 allow limited separation of adjacent turns of the coil (A–A', or B–B'), hence the flexibility. In the embodiment of the present invention depicted in FIG.7(a)–7(b), there are two sets of connectors between any pair of adjacent turns of the coil; in opposite directions and on opposite sides of the stent. In another configuration, the connectors 36 would all be parallel and all on the same side of the stent, with one connector 36 per turn. Variations in the width, length, direction, and number of these oblique connectors 36 can be used to adjust the flexibility and longitudinal stability of the stent.

It will be further apparent to one skilled in this art that the improvements provided for in the present invention, while described with relation to certain specific physical embodiments also lend themselves to being applied in other physical arrangements not specifically provided for herein, which are nonetheless within the spirit and scope of the invention taught here.

I claim:

1. An expandable stent with improved structural stability for insertion into a corporeal lumen, the stent having a longitudinal axis and comprising a helically coiled ribbon, the stent expandable from a compressed configuration to an expanded configuration, the coiled ribbon comprising a single strip of metal helically wound around the longitudinal axis of the stent, the strip of metal having a plurality of interconnected parallel zigzag chains, each chain running the length of the single strip of metal and joined to adjacent zigzag chains, each zigzag chain comprising a sense of struts, the struts at their ends adjoined to adjacent struts by connections, the connections on one side of the zigzag chains being the common connections for the adjacent side of an adjacent zigzag chain, the struts of each zigzag chain being approximately parallel to adjacent struts when the stent is in a compressed configuration, and the struts being at angles to adjacent struts when the stent is in an expanded configuration.

2. The expandable stent according to claim 1, wherein the normal configuration of the stent is the expanded configuration and the stent is self-expanding and is inserted as a corporeal lumen in the compressed configuration.

3. The expandable stent according to claim 2 wherein the stent is self-expanding.

4. The expandable stent according to claim 1, wherein the normal configuration of the stent is the compressed configuration and the stent is expanded by balloon expanding.

5. The expandable stent according to claim 1 wherein the helically coiled ribbon is sufficiently rigid to maintain the relative position of each turn of each coil of the helically coiled ribbon during expansion of the stent within the corporeal lumen and wherein the diameter of the expandable helically coiled ribbon increases during expansion of the stent without any substantial change in the overall longitudinal length of the stent and in the number of turns of the helically coiled ribbon.

6. The expandable stent according to claim 1 wherein the axial orientation of the helically coiled ribbon remains substantially constant relative to the longitudinal axis of the stent during expansion of the stent from the compressed configuration to the expanded configuration.

7. The expandable stent according to claim 1 wherein a single strip of metal has been etched to form a lattice of the interconnected parallel zigzag chains.

8. The expandable stent according to claim 1 wherein the single strip of metal is a lattice comprised of the interconnected parallel zigzag chains, the lattice appearing when viewed flat in the stent's compressed configuration as an alternating series of offset transverse elongated slots in the single strip of metal.

9. The expandable stent according to claim 1 wherein the single strip of metal is a lattice comprised of the parallel interconnected zigzag chains, the lattice appearing when viewed flat in the stent's expanded configuration as a series of interconnected parallel zigzag chains, each chain comprising a series of longitudinal struts joined at their ends to form the connections.

10. The expandable stent according to claim 1 wherein the single strip of metal has a lattice structure, the lattice appearing when viewed flat in the stent's expanded configuration as a series of interconnected parallel zigzag chains, each chain comprising the struts connected at their ends to form connections, and a layer of longer, more rigid longitudinal struts which extend from one edge of the single strip of metal to the other edge, the layer of longer, more rigid longitudinal struts superimposed on alternate struts or each zigzag chain.

11. The expandable stent according to claim 1 wherein each coil of the helically coiled ribbon is joined to the adjacent coil.

12. The expandable stent according to claim 1 wherein the stent has been formed by etching one or more spiral slots into a cylinder of metal, at least one spiral slot extending the length of the cylinder of metal to form the single strip of metal helically wound around the longitudinal axis of the stent.

13. The expandable stent according to claim 1 wherein the stent is formed by etching one or more spiral slots into a cylinder of metal, each spiral slot terminating before it exits the end of the metal cylinder, to form the single string of metal helically wound around the longitudinal axis of the stent.

14. The expandable stent according to claim 1 wherein the stent is formed by etching a plurality of offset and overlapping spiral slots into a cylinder of metal in order to form a series of parallel slots and at least one series of parallel connectors between each coil of the helically coiled ribbon.

15. An expandable stent with improved structural stability for insertion into a corporeal lumen, the stent having a longitudinal axis and comprising a helically coiled ribbon, the stent expandable from a compressed configuration to an expandable configuration, the coiled ribbon comprising a single strip of metal helically wound around the longitudinal axis of the stent, the single strip of metal comprising a plurality of interconnected parallel zigzag chains, each chain running the length of the single strip of metal, and joined to adjacent zigzag chains, each chain comprising a series of struts, the struts at their ends joined to adjoining struts by connections, the connections on adjacent sides of adjacent zigzag chains being joined by longitudinal spacers to join the adjacent zigzag chains, the longitudinal spacer perpendicular to the zigzag chains, the struts of each zigzag chain being approximately parallel to adjacent struts when the stent is in a compressed configuration, and the struts positioned at an angle to adjacent struts when the stent is in an expanded configuration.

16. The expandable stent according to claim 15, wherein the normal configuration of the stent is the expanded configuration and the stent is self-expanding and is inserted as a corporeal lumen in the compressed configuration.

17. The expandable stent according to claim 15 wherein the stent is self-expanding.

18. The expandable stent according to claim 15, wherein the normal configuration of the stent is the compressed configuration and the stent is expanded by balloon expanding.

19. The expandable stent according to claim 15 wherein the helically coiled ribbon is sufficiently rigid to maintain the relative position of each coil of the helically coiled ribbon during expansion of the stent within the corporeal lumen and wherein the diameter of the extendible helically coiled ribbon increases during expansion of the stent without any substantial change in the overall longitudinal length of the stent and in the number of turns of the helically coiled ribbon.

20. The expandable stent according to claim 15 wherein the axial orientation of the helically coiled ribbon remains substantially constant relative to the longitudinal axis of the stent during expansion of the stent from the compressed configuration to the expanded configuration.

21. The expandable stent according to claim 15 wherein the single strip of metal has an etched lattice of the interconnected parallel zigzag chains.

22. The expandable stent according to claim 15 wherein the single strip of metal is a lattice comprised of the interconnected parallel zigzag chains, the lattice appearing when viewed flat in the stent's compressed configuration as an alternating series of offset transverse elongated slots in the single strip of metal.

23. The expandable stent according to claim 15 wherein the single strip of metal is a lattice comprised of the interconnected parallel zigzag chains, the lattice appearing when viewed flat in the stent's expanded configuration as a series of interconnected parallel zigzag chains, each chain comprising a series of longitudinal struts joined at their ends to form connections.

24. The expandable stent according to claim 15 wherein the single strip of metal is a lattice, the lattice appearing when viewed flat in the stent's expanded configuration as a series of interconnected parallel zigzag chains, each chain comprising struts connected at their ends to form connections, a layer of longer and more rigid longitudinal struts which extend from one edge of the single strip of metal to the other edge, the layer of longer, more rigid longitudinal struts superimposed on alternate struts of each zigzag chain.

25. The expandable stent according to claim 15 wherein each end coil of the helically coiled ribbon is joined to the adjacent coil.

26. The expandable stent according to claim 15 wherein the stent is formed by etching a plurality of offset and overlapping spiral slots into a cylinder of metal in order to form a series of parallel slots and at least one series of parallel connectors between each coil of the helically coiled ribbon.

* * * * *